US 6,844,196 B2

(12) United States Patent
King et al.

(10) Patent No.: US 6,844,196 B2
(45) Date of Patent: Jan. 18, 2005

(54) ANALYSIS OF ANTIOXIDANT IN SOLDER PLATING SOLUTIONS USING MOLYBDENUM DICHLORIDE DIOXIDE

(75) Inventors: Mackenzie E. King, Southbury, CT (US); Cory Schomburg, Leander, TX (US); Monica K. Hilgarth, Oxford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 57 days.

(21) Appl. No.: 10/320,875

(22) Filed: Dec. 17, 2002

(65) Prior Publication Data

US 2003/0143753 A1 Jul. 31, 2003

Related U.S. Application Data

(60) Provisional application No. 60/344,074, filed on Dec. 28, 2001.

(51) Int. Cl.$^7$ ......................... G01N 33/00; G01N 21/75; G01N 33/20

(52) U.S. Cl. ..................... 436/131; 422/61; 422/68.1; 422/81; 422/82.05; 422/82.09; 436/73; 436/166; 436/171

(58) Field of Search ........................... 422/61, 68.1, 81, 422/82.05, 82.09; 436/73, 77, 131, 166, 171

(56) References Cited

U.S. PATENT DOCUMENTS 4,640,746 A * 2/1987 Nobel et al. ................ 205/123
5,219,484 A * 6/1993 Krulik ........................ 252/79.2
5,294,554 A * 3/1994 Uchida et al. ............... 436/73

OTHER PUBLICATIONS

Halmekoski, J. Suomen Kemistilehti 1959, 32, 274–276.*
Barnum, D. W. Analytica Chimica Acta 1977, 89, 157–166.*
Yokoi, K. et al, Polyhedron 1993, 12, 911–914.*
Questel, J.H. "A Colour Test for o–Dihydroxy–Phenols" The Analyst May 1931, vol. 56, No. 662, p. 311.
Chemical Abstracts, vol. 54, No. 22, issued Nov. 25, 1960, Halmekoski, J., "Spectrophotometric Determination of Catechol, Quinone, and Resorcinol in Aqueous Solutions" see column 24129, abstract g, Suomen Kemistilchti 1959, 32, 273–276.
Barnum, D.W. "Spectrophotometric Determination of Catechol, Ephinephrine, Dopa. Dopamine and Other Aromatic Vic–Diols" Analytica Chimica Acta 1977, vol. 89, pp. 157–166.
Will, F., et al., "Colorimetric Determination of Molybdenum with Disodium–1,2–Dihydroxybenzene–3,5–D–sulfonate" Analytica Chimica Acta 1953, vol. 8, pp. 546–557.
Buchwald, H. et al., "The Colorimetric Determination of Molybdenum with Polyhdyric Phenols" Talanta 1962, vol. 9, pp. 631–637.
Chemical Abstracts, vol. 77, No. 20, isued Nov. 13, 1972, Soni, N.R. et al., "Determination of Molybdenum(VI) and o–Diphenols by High Frequency Titrations" see abstract 134652n, Indian Journal of Chemistry, 1972, 10(4), 446–447.

(List continued on next page.)

Primary Examiner—Arlen Soderquist
(74) Attorney, Agent, or Firm—Margaret Chappuis; Steven Hultquist, Esq.

(57) ABSTRACT

The present invention relates to antioxidant analysis for solder plating solutions, by using a complexing solution comprising a molybdenum compound, such as $MoO_2Cl_2$, to form a highly colored antioxidant-molybdenum complex, which can be detected and analyzed by UV-Vis spectroscopic, as a basis for concentration determination for the antioxidant.

10 Claims, 5 Drawing Sheets

OTHER PUBLICATIONS

Singh, A.K., et al., "Spectrophotometric Determination of Molybdenum in Steels with Pyrocatechol and Neotetrazolium Chloride" Analyst, Jun. 1985, vol. 110, pp. 751–753.

Kustin, K., et al., "Kinetics and Complex Formation of Molybdate with Catechol" Journal of The American Chemical Society, Apr. 18, 1973, vol. 95, No. 8, pp. 2487–2491.

Yamahara, R., et al. Inorg. Chim Acta 2000, 300–302, 587, "(Cateholato) iron (III) complexes with tetradentate tripodal ligands containing substituted phenol and pyridine units as structural and functional model complexes for the catechol–bound intermediate of intradiol–cleaving catechol dioxygenases".

Funabiki, T., et al. Chem. Lett. 1989, 1267 "Catalytic hydroxylation of aromatic compounds with oxygen by a catecholatoiron complex in acetonitrile usin ghydroquinones as reductants".

Funabiki, T., et al. J. Chem.Soc.Commun. 1986, 1699 "Spectroscopic evidence for the formation of catecholato–iron(III) and semiquinonato–iron (II) pyridine complexes in the oxygenation of catechol by a pyridineiron(III) complex".

* cited by examiner

US 6,844,196 B2

ANALYSIS OF ANTIOXIDANT IN SOLDER PLATING SOLUTIONS USING MOLYBDENUM DICHLORIDE DIOXIDE

CROSS-REFERENCE TO RELATED APPLICATIONS

This application claims priority to U.S. Provisional Patent Application No. 60/344,074 filed on Dec. 28, 2001 and entitled "ANALYSIS OF RD IN SOLDERON PLATING BATH SOLUTIONS USING MOLYBDENUM DICHLORIDE DIOXIDE."

BACKGROUND OF THE INVENTION

1. Field of Invention

The present invention relates generally to antioxidant analysis for solder plating solutions, and more specifically, to a system and method for determining the concentration of antioxidant in solder plating solutions.

2. Related Art

Solder plating solutions contain a variety of organic additives, which are important for improving the plating quality and preventing formation of solder bumps on the plate surface.

Antioxidant additive, such as catechol, is usually added into solder plating solutions, for preventing oxidation of the divalent tin ($Sn^{2+}$) ions from being oxidized to tetravalent $Sn^{4+}$ ions by oxygen dissolved in the solder plating solutions. It is necessary to monitor the concentration of such antioxidant additive in the solder plating solutions and to replenish such additive when it becomes depleted over time.

Currently, accurate, on-line analysis of the antioxidant (catechol) concentration in high-lead solder plating solutions is still impossible, due to the fact that the presence of lead, tin, and methane sulfonic acid (MSA) has a significant matrix effect on the measurement of the antioxidant concentration, i.e., concentration variations of lead, tin, and methane sulfonic acid affect the measurement results obtained for the antioxidant.

It is therefore an object of the present invention to provide a method for quick and accurate on-line analysis of the antioxidant concentration in solder plating solutions, which minimize the matrix effect from lead, tin, and methane sulfonic acid concentration variation.

Other objects and advantages will be more fully apparent from the ensuring disclosure and appended claims.

SUMMARY OF THE INVENTION

The present invention in one aspect relates to a method for determining concentration of antioxidant in a sample solder plating solution, comprising the steps of:

(a) providing a complexing solution comprising at least one molybdenum compound;

(b) adding the sample solder plating solution into the complexing solution, so as to form an antioxidant-molybdenum complex that is detectable by UV-Vis spectroscopy;

(c) conducting UV-Vis absorption analysis at a wavelength that maximizes UV absorbance of the antioxidant-molybdenum complex; and (d) determining the antioxidant concentration in the sample solder plating solution, based on the UV-Vis absorption analysis result.

Another aspect of the present invention relates to a system for measuring concentration of antioxidant in a sample solder plating solution, comprising:

(a) a fluid compartment containing a complexing solution comprising at least one molybdenum compound;

(b) a sample solution inlet for introducing the sample solder plating solution into the complexing solution contained by the fluid compartment, so as to form therein an antioxidant-molybdenum complex that is detectable by UV-Vis spectroscopy;

(c) a UV-Vis spectrometer constructed and arranged for conducting absorption analysis of the antioxidant-molybdenum complex, at a wavelength that maximizes UV absorbance thereof; and (d) a computational device connected with the UV-Vis spectrometer, for determining the antioxidant concentration in such sample solder plating solution, based on the UV-Vis absorption analysis result.

Additional aspects, features and embodiments of the invention will be more fully apparent from the ensuring disclosure and appended claims.

Figure 5:
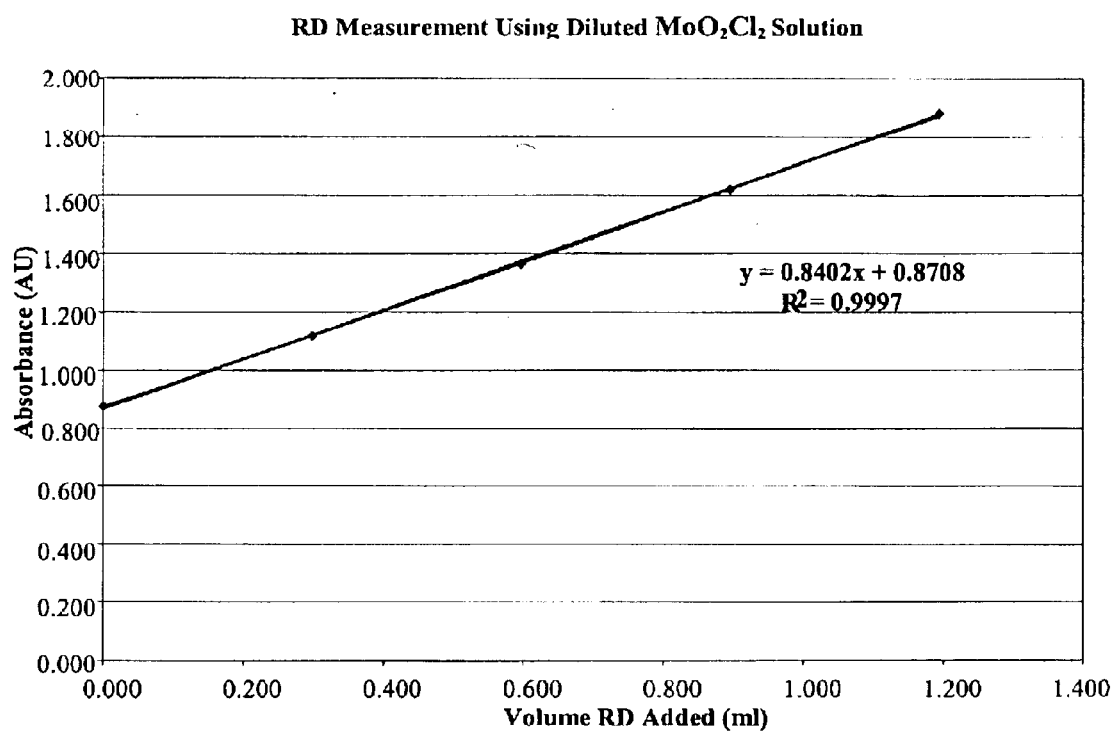
FIG. 5 is a graph plotting the absorbance measured by a UV-Vis spectrometer as a linear function of the volume of a dilute standard antioxidant solution added, while such standard antioxidant solution comprises ethanolamine.

As a specific example, UV-Vis spectroscopic analysis of antioxidant concentration of a sample high lead solder plating solution, which comprises $Sn^{2+}$, $Pb^{2+}$, MSA, and antioxidant at a concentration of about 10 ml/L. Such analysis was performed using 1.5 ml of the sample high lead solder plating solution, and the above-described $MoO_2Cl_2$/$NH_4C_2H_3O_2$/EDTA solution as diluted in water, with 0.25 ml neat ethanolamine added therein. A calibration curve as shown in FIG. 5 was constructed to quantify the relationship between the antioxidant concentration and the absorbance measured, by adding a standard antioxidant solution with 0.3 ml increment. The correlation coefficient R of such calibration curve is close to 1 ($0.9997^{0.5}=0.9998$), with further improved correlation between the absorbance and the antioxidant concentration in the sample solution.

DETAILED DESCRIPTION OF THE INVENTION, AND PREFERRED EMBODIMENTS THEREOF

Molybdenum (VI) dichloride dioxide ($MoO_2Cl_2$) liberates $Cl_2$ gas in aqueous solutions, and presents binding sites for phenolic organic compounds, including the catechol group that constitutes antioxidant additives in solder plating solutions.

Complexing of the antioxidant catechol with $MoO_2Cl_2$ results in a yellow-orange colored complex that can be readily analyzed by UV-Vis spectroscopy.

Figure 1:
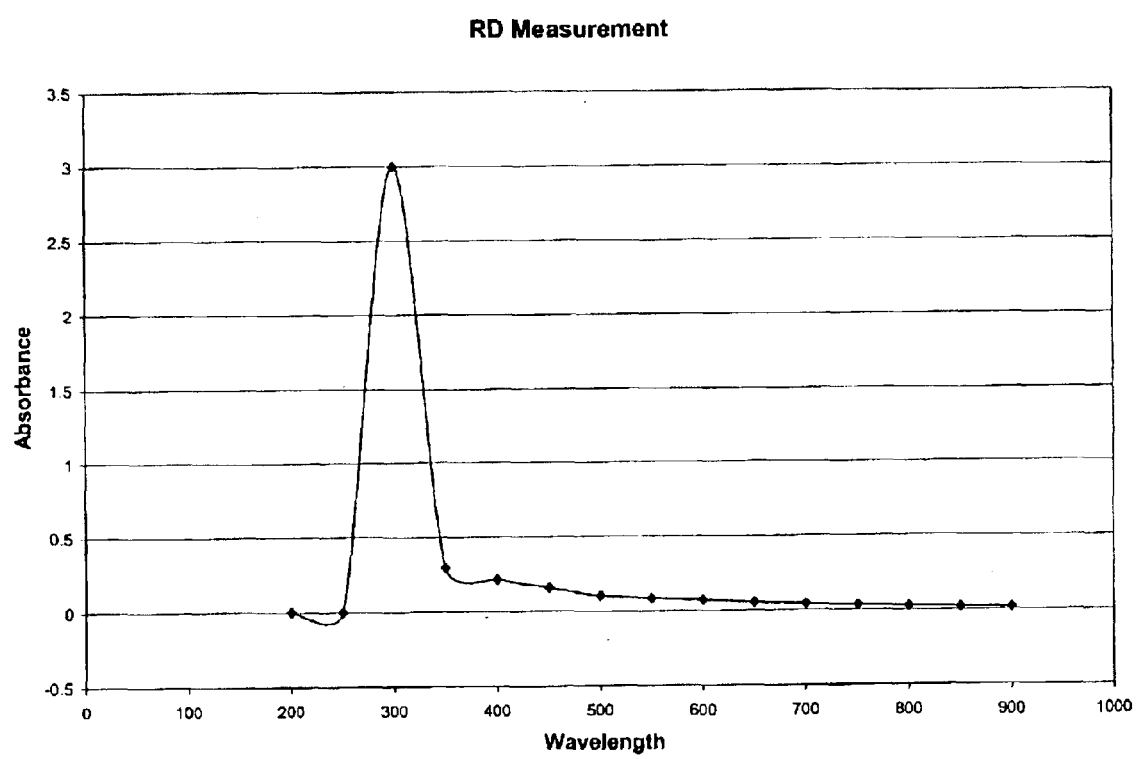
FIG. 1 depicts the UV-Vis absorption spectrum of antioxidant-molybdenum complex in a mixed solution formed by adding an antioxidant solution into a complexing solution comprising molybdenum dichloride dioxide, ethylenediaminetetraacetate (EDTA), and ammonium acetate.

As an initial test to find the absorbance maximum of this complex, 15 ml of an aqueous solution comprising $MoO_2Cl_2$, EDTA, and ammonium acetate was added to a beaker and stirred. To this aqueous solution, several drops of antioxidant concentrate were added, to form a mixed solution comprising a highly colored antioxidant-molybdenum complex. A UV-Vis absorbance spectrum of the colored antioxidant-molybdenum complex was obtained by using a UV-Vis spectrometer, which is provided in FIG. 1. The antioxidant-molybdenum complex shows a maximum absorbance at a wavelength in a range of from about 280 nm to about 320 nm, and approximately 300 nm.

Manipulation of the pH value of the mixed solution that contains the colored antioxidant-molybdenum complex can change the absorption coefficient of the complex. It was discovered by the inventors of the present invention that addition of an ethanolamine solution to the $MoO_2Cl_2$ solution vastly enhances the absorption coefficient of the antioxidant-molybdenum complex, as indicated by the absorption spectrum shown in FIG. 2.

Figure 2:
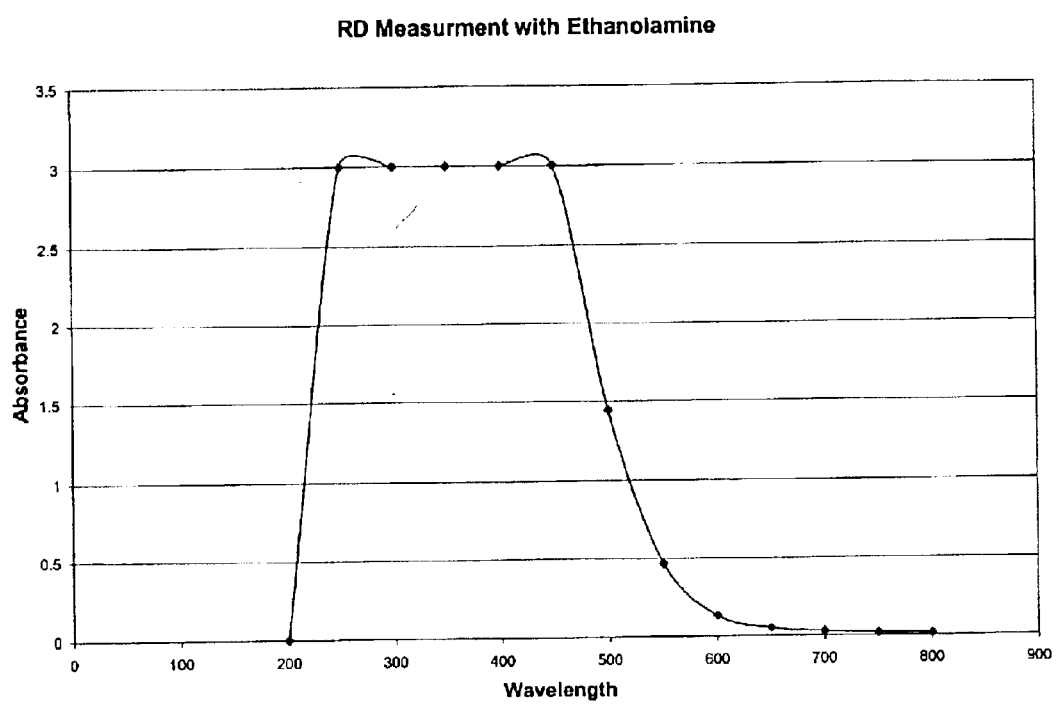
FIG. 2 depicts the UV-Vis absorption spectrum of antioxidant-molybdenum complex in an antioxidant solution formed by adding a sample solder plating solution into a complexing solution comprising molybdenum dichloride dioxide, EDTA, ammonium acetate, and ethanolamine.

From the absorption spectrum in FIG. 2, it can be seen that addition of the ethanolamine vastly increases the absorption coefficient, allowing for lower limits of detection to be observed. The antioxidant-molybdenum complex in the ethanolamine-containing solution shows a maximum absorbance at a wavelength in a range of from about 280 nm to about 420 nm, and preferably from 300 nm to about 400 nm.

Figure 3:
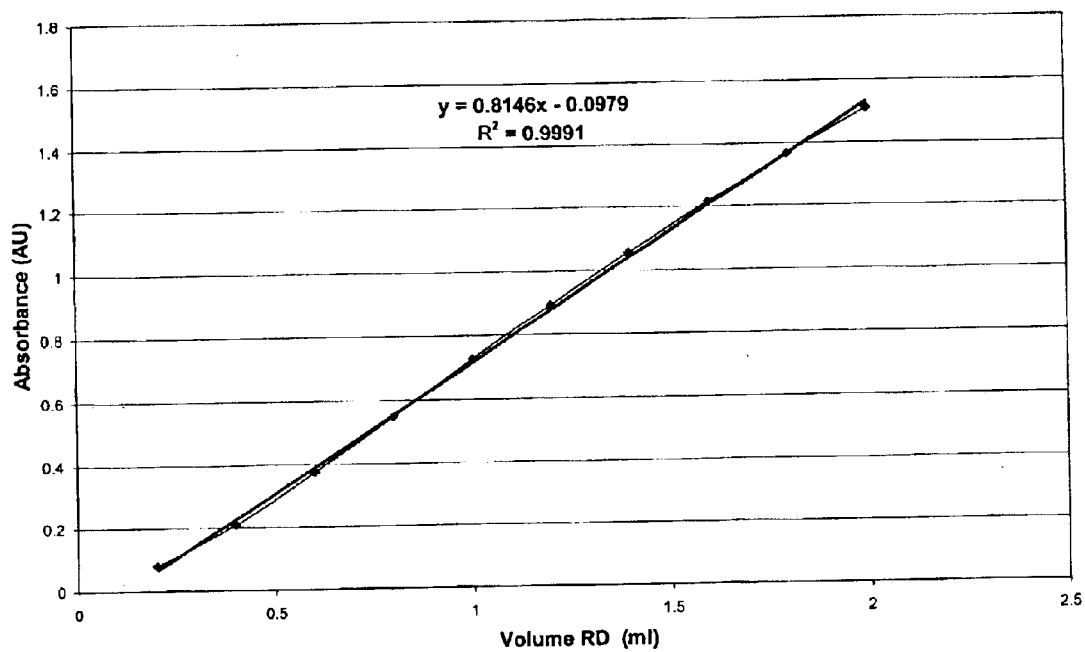
FIG. 3 is a graph plotting the absorbance measured by a UV-Vis spectrometer as a linear function of the volume of a standard antioxidant solution added.

The linearity between the absorbance of antioxidant-molybdenum complex and the concentration thereof was next investigated. 15 ml of the solution comprising $MoO_2Cl_2$, EDTA, and ammonium acetate was added to a beaker and stirred. To this solution, antioxidant concentrate was added in 0.2 ml increments, and the absorbance of the antioxidant-molybdenum complex was measured at approximately 300 nm using a UV-Vis spectrometer. A graph was plotted, which depicts the absorbance measured as a linear function of the volume of antioxidant concentrate added, as shown in FIG. 3. FIG. 3 shows that the correlation coefficient R between the absorbance and the antioxidant added is very close to 1 ($0.9991^{0.5}=0.9995$), indicating almost perfect correlation therebetween, consistent with Beer's law.

Figure 4:
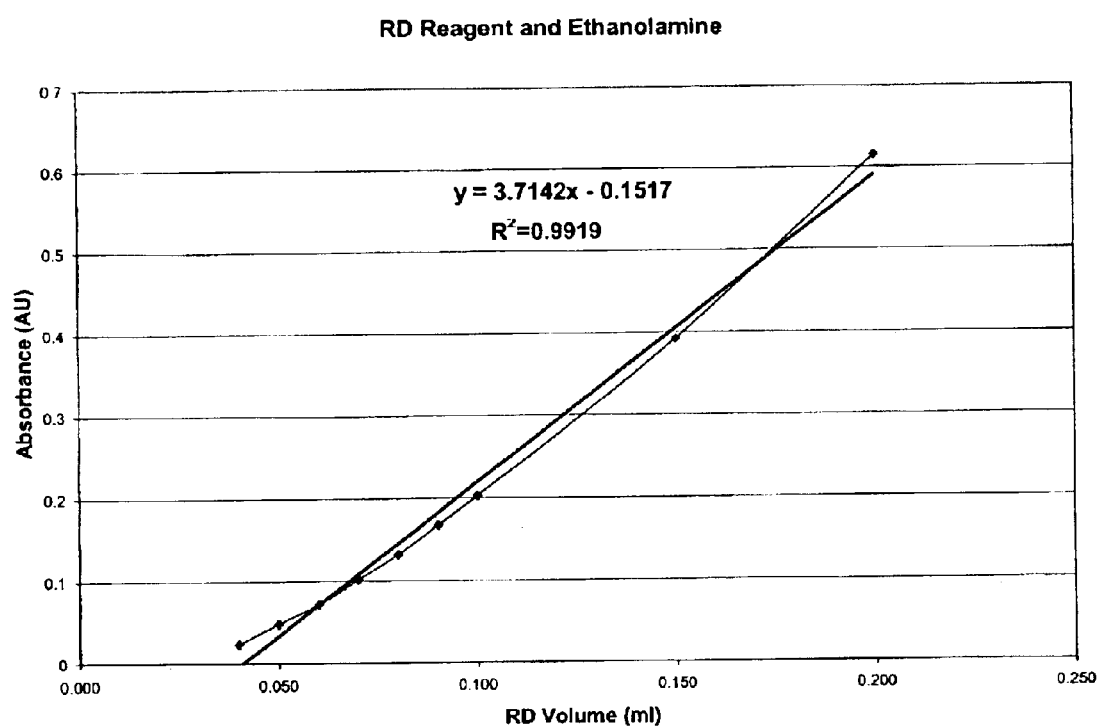
FIG. 4 is a graph plotting the absorbance measured by a UV-Vis spectrometer as a linear function of the volume of a standard antioxidant solution added, while such standard antioxidant solution comprises ethanolamine.

FIG. 4 shows that another graph that plots the absorbance measured at approximately 330 nm as a linear function of the volume of antioxidant concentrate added, wherein the pH of the solution was adjusted using ethanolamine, and wherein the antioxidant additions were made in 0.01 ml increments, starting with an initial dose of 0.04 ml antioxidant. An overall linear correlation exits between the absorbance and the antioxidant added, with a correlation coefficient R close to 1 ($0.9919^{0.5}=0.996$), indicating almost perfect correlation therebetween. In FIG. 4, it can be seen that at very low concentration of antioxidant, a slightly non-linear region exists. This non-linear region appears to exist between 0.040 and 0.070 ml of the antioxidant concentrate. This non-linear region has very little effect on the overall measurement results for antioxidant concentration, since the measured sample solder plating solutions usually contain antioxidant at a concentration much higher than that of such non-linear region.

Therefore, the UV-Vis spectroscopic analysis of the sample solder plating solutions using molybdenum dichloride dioxide as a complexing agent, as contemplated by the present invention, is suitable for determining the antioxidant concentration in such sample solution.

Problems associated with the presence of tin and lead in the solder plating solution are overcome with the addition of EDTA. To successfully analyze the antioxidant concentration, ammonium acetate is also added to buffer the solution and produce the desired pH range for analysis.

At high concentrations of molybdenum, a significant drift in the absorption measurements was observed, which reduces the accuracy of the UV-Vis spectrometric analysis. Such drift can be effectively reduced by diluting the $MoO_2Cl_2/NH_4C_2H_3O_2/EDTA$ solution by 4 or 5 times, using water and 2M ethanolamine solution. Experiments showed that such dilution can effectively reduce the drift in the absorption measurements to about 0.02 absorbance unit (AU) over a five minute period.

As a specific example, UV-Vis spectroscopic analysis of antioxidant concentration of a sample high lead solder plating solution, which comprises $Sn^{2+}$, $Pb^{2+}$, MSA, and antioxidant at a concentration of about 10 ml/L. Such analysis was performed using 1.5 ml of the sample high lead solder plating solution, and the above-described $MoO_2Cl_2/NH_4C_2H_3O_2/EDTA$ solution as diluted in water, with 0.25 ml neat ethanolamine added therein. A calibration curve as shown in FIG. 5 was constructed to quantify the relationship between the antioxidant concentration and the absorbance measured, by adding a standard antioxidant solution with 0.3 ml increment. The correlation coefficient R of such calibration curve is close to 1 ($0.9997^{0.5}=0.9998$), with further improved correlation between the absorbance and the antioxidant concentration in the sample solution.

The present method for determining the antioxidant concentration in a sample solder plating solution overcomes the background interference from tin, lead, and brightener in such sample solution, and allows accurate determination of antioxidant concentration.

The method of the present invention can be performed by a system comprising a fluid compartment containing a complexing solution comprising a molybdenum compound such as $MoO_2Cl_2$; a sample solution inlet for introducing a sample solder plating solution into the complexing solution contained by said fluid compartment, so as to form therein an antioxidant-molybdenum complex that is detectable by UV-Vis spectroscopy; a UV-Vis spectrometer constructed and arranged for conducting absorption analysis of said antioxidant-molybdenum complex, at a wavelength that maximizes UV absorbance thereof; and a computational device connected with said UV-Vis spectrometer, for determining the antioxidant concentration in said sample solder plating solution, based on the UV-Vis absorption analysis result. Such computational device may comprise a general-purpose programmable computer, central processing unit (CPU), microprocessor, integrated circuitry, computational module, or the like, which is constructed, operated and arranged to determine the antioxidant concentration.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A method for determining concentration of antioxidant in a sample solder plating solution, comprising the steps of:
   (a) providing a complexing solution comprising molybdenum dichloride dioxide, a binding agent for complexing with tin and lead ions in said sample solder plating solution, and a buffering agent for stabilizing pH value of said sample solder plating solution;
   (b) adding the sample solder plating solution into said complexing solution, so as to form an antioxidant-molybdenum complex that is detectable by UV-Vis spectroscopy;
   (c) conducting UV-Vis absorption analysis at a wavelength that maximizes UV absorbance of said antioxidant-molybdenum complex; and
   (d) determining the antioxidant concentration in said sample solder plating solution, based on the UV-Vis absorption analysis result.

2. The method of claim 1, wherein the UV-Vis absorption analysis is conducted at a wavelength in a range of from about 280 nm to about 420 nm.

3. The method of claim 1, wherein the UV-Vis absorption analysis is conducted at a wavelength in a range of from about 300 nm to about 400 nm.

4. The method of claim 1, wherein the binding agent is EDTA.

5. The method of claim 4, wherein the buffering agent is ammonium acetate.

6. The method of claim 5, wherein ethanolamine is added to said complexing solution before addition of the sample solder plating solution thereinto.

7. A system far measuring concentration of antioxidant in a sample solder plating solution, comprising:
   (a) a fluid compartment containing a complexing solution comprising molybdenum dichloride dioxide, a binding agent for complexing with tin and lead ions in said sample solder plating solution, and a buffering agent for stabilizing pH value of said sample solder plating solution;
   (b) a sample solution inlet for introducing the sample solder plating solution into the complexing solution contained by said fluid compartment, so as to form therein an antioxidant-molybdenum complex that is detectable by UV-Vis Spectroscopy,
   (c) a UV-Vis spectrometer constructed and arranged for conducting absorption analysis of said antioxidant-molybdenum complex, at a wavelength that maximizes UV absorbance thereof; and
   (d) a computational device connected with said UV-Vis spectrometer, for determining the antioxidant concentration in said sample solder plating solution, based on the UV-Vis absorption analysis result.

8. The system of claim 7, wherein the binding agent is EDTA.

9. The system of claim 8, wherein the buffering agent is ammonium acetate.

10. The system of claim 9, wherein the complexing solution further comprises ethanolamine.

* * * * *